(12) United States Patent
Weiner et al.

(10) Patent No.: US 10,195,061 B2
(45) Date of Patent: Feb. 5, 2019

(54) CONTROLLED TISSUE INGROWTH STENT COVERING

(71) Applicant: BOSTON SCIENTIFIC SCIMED, INC., Maple Grove, MN (US)

(72) Inventors: Jason Weiner, Grafton, MA (US); Sean P. Fleury, Brighton, MA (US); Gary J. Leanna, Holden, MA (US); Seamus F. O'Shaughnessy, Chelmsford, MA (US); Dane T. Seddon, Boston, MA (US)

(73) Assignee: BOSTON SCIENTIFIC SCIMED, INC., Maple Grove, MN (US)

(\*) Notice: Subject to any disclaimer, the term of this patent is extended or adjusted under 35 U.S.C. 154(b) by 11 days.

(21) Appl. No.: 14/919,688

(22) Filed: Oct. 21, 2015

(65) Prior Publication Data

US 2016/0113788 A1 Apr. 28, 2016

Related U.S. Application Data (60) Provisional application No. 62/067,177, filed on Oct. 22, 2014.

(51) Int. Cl.
| | |
|---|---|
| *A61F 2/04* | (2013.01) |
| *A61F 2/89* | (2013.01) |
| *A61F 2/00* | (2006.01) |
| *A61F 2/07* | (2013.01) |
| *A61F 2/848* | (2013.01) |

(52) U.S. Cl.
CPC .............. *A61F 2/89* (2013.01); *A61F 2/0077* (2013.01); *A61F 2/04* (2013.01); *A61F 2/07* (2013.01); *A61F 2/848* (2013.01); *A61F 2002/046* (2013.01); *A61F 2230/0069* (2013.01)

(58) Field of Classification Search
CPC ........ A61F 2/04; A61F 2/07; A61F 2002/046; A61F 2002/041; A61F 2002/043; A61F 2002/044; A61F 2/0077; A61F 2220/005; A61F 2002/30448
See application file for complete search history.

(56) References Cited

U.S. PATENT DOCUMENTS

| | | | | |
|---|---|---|---|---|
| 4,047,252 A | * | 9/1977 | Liebig | A61F 2/06 623/1.34 |
| 5,330,500 A | | 7/1994 | Song | |
| 6,156,064 A | * | 12/2000 | Chouinard | A61F 2/07 623/1.44 |
| 6,547,820 B1 | * | 4/2003 | Staudenmeier | A61F 2/06 264/103 |
| 7,921,678 B2 | * | 4/2011 | Norris | A61F 2/07 66/195 |
| 8,197,529 B2 | | 6/2012 | Cully et al. | |

(Continued)

*Primary Examiner* — Dinah Baria
(74) *Attorney, Agent, or Firm* — Seager, Tufte & Wickhem, LLP (57) ABSTRACT

A stent covering includes a polymeric tube having a first end, a second end and a length extending therebetween, the polymeric tube including an inner surface defining a lumen and an outer surface. A plurality of tissue ingrowth features are formed on the outer surface of the polymeric tube, at least some of the plurality of tissue ingrowth features including polymeric loops that extend above the outer surface such that, once implanted, tissue can grow between the outer surface and the polymeric loops. A stent may include such a stent covering.

20 Claims, 8 Drawing Sheets

(56) References Cited

U.S. PATENT DOCUMENTS

| | | |
|---|---|---|
| 8,209,843 B2 * | 7/2012 | Thistle ............... A61F 2/07 29/433 |
| 8,435,283 B2 | 5/2013 | Jordan et al. |
| 8,916,227 B2 | 12/2014 | Horres et al. |
| 8,974,522 B2 | 3/2015 | Bates et al. |
| 2002/0052649 A1 | 5/2002 | Greenhalgh |
| 2002/0099441 A1 * | 7/2002 | Dehdashtian ......... A61F 2/07 623/1.51 |
| 2005/0125020 A1 | 6/2005 | Meade et al. |
| 2009/0187240 A1 | 7/2009 | Clerc et al. |
| 2012/0035715 A1 | 2/2012 | Robida et al. |
| 2013/0138219 A1 | 5/2013 | Toomey et al. |
| 2013/0184808 A1 | 7/2013 | Hall et al. |
| 2013/0268063 A1 | 10/2013 | Firstenberg et al. |
| 2014/0277395 A1 | 9/2014 | Firstenberg et al. |
| 2014/0277442 A1 | 9/2014 | Seddon et al. |
| 2015/0051693 A1 | 2/2015 | Bertolino et al. |
| 2015/0342760 A1 | 12/2015 | Christakis et al. |

* cited by examiner

CONTROLLED TISSUE INGROWTH STENT COVERING

CROSS-REFERENCE TO RELATED APPLICATIONS

This application claims priority under 35 U.S.C. § 119 to U.S. Provisional Application Ser. No. 62/067,177, filed Oct. 22, 2014, the entirety of which is incorporated herein by reference.

TECHNICAL FIELD

The disclosure is directed to a covering for an endoprosthesis, such as a stent. More particularly, the disclosure is directed to a stent covering having anti-migration features formed within the stent covering.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered stents, on the other hand, prevent tissue ingrowth to facilitate removal. However, fully covered endoprostheses are prone to migrate through the body lumen.

Accordingly, it is desirable to provide endoprostheses that exhibit anti-migration features, while reducing the trauma to the body lumen of the patient if removal of the endoprosthesis is desired.

BRIEF SUMMARY

The disclosure is directed to several alternative designs, materials and methods of manufacturing medical device structures and assemblies, and uses thereof.

In one example, a stent covering includes a polymeric tube having a first end, a second end and a length extending therebetween, the polymeric tube including an inner surface defining a lumen and an outer surface. A plurality of tissue ingrowth features are formed on the outer surface of the polymeric tube, at least some of the plurality of tissue ingrowth features including polymeric loops that extend above the outer surface such that, once implanted, tissue can grow between the outer surface and the polymeric loops.

Alternatively, or additionally, at least some of the tissue ingrowth features are integrally molded as part of the polymeric tube.

Alternatively, or additionally, the polymeric tube includes silicone.

Alternatively, or additionally, at least some of the polymeric loops include an arcuate arch that is connected at opposing ends to the outer surface of the polymeric tube and that has an intermediate portion that is not directly connected to the outer surface of the polymeric tube.

Alternatively, or additionally, at least some of the polymeric loops are oriented transversely to the length of the polymeric tube.

Alternatively, or additionally, at least some of the polymeric loops are oriented at an acute angle relative to the length of the polymeric tube.

In another example, a stent assembly includes a metal stent extending from a first end to a second end, the metal stent including an inner stent surface defining a stent lumen extending therethrough, and an outer stent surface. A polymeric covering extends over the outer stent surface and has an inner surface in contact with the outer stent surface and an outer surface. A plurality of tissue ingrowth features are formed on the outer surface of the polymeric covering, at least some of the plurality of tissue ingrowth features including polymeric loops that extend above the outer surface of the polymeric covering such that, once implanted, tissue can grow between the outer surface and the polymeric loops. The polymeric covering prevents tissue ingrowth into the metal stent lumen.

Alternatively, or additionally, the metal stent includes a braided stent.

Alternatively, or additionally, the metal stent includes an expandable metal stent.

Alternatively, or additionally, at least some of the tissue ingrowth features are integrally molded as part of the polymeric covering.

Alternatively, or additionally, the polymeric covering includes silicone.

Alternatively, or additionally, at least some of the polymeric loops includes an arcuate arch that is connected at opposing ends to the outer surface of the polymeric covering and that has an intermediate portion that is not directly connected to the outer surface of the polymeric covering.

Alternatively, or additionally, at least some of the polymeric loops are oriented transversely to the length of the metal stent.

Alternatively, or additionally, at least some of the polymeric loops are oriented at an acute angle relative to the length of the metal stent.

In another example, an airway stent configured for long term placement within a patient's trachea includes a metal support structure extending from a first end to a second end, the metal support structure including an surface defining an airway stent lumen extending therethrough, and an outer surface. A polymeric covering extends over the outer surface and includes a plurality of tissue ingrowth features extending outwardly from the polymeric covering, at least some of the plurality of tissue ingrowth features including polymeric loops that extend above the outer surface of the polymeric covering such that, once implanted, tissue can grow between the outer surface and the polymeric loops. The polymeric covering prevents tissue ingrowth into the airway stent lumen.

Alternatively, or additionally, at least some of the tissue ingrowth features are integrally molded as part of the polymeric covering.

Alternatively, or additionally, the polymeric covering includes silicone.

Alternatively, or additionally, at least some of the polymeric loops include an arcuate arch that is connected at opposing ends to the outer surface of the polymeric covering and that has an intermediate portion that is not directly connected to the outer surface of the polymeric covering.

Alternatively, or additionally, at least some of the polymeric loops are oriented transversely to a length of the metal support structure.

Alternatively, or additionally, at least some of the polymeric loops are oriented at an acute angle relative to a length of the metal support structure.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly indicated to the contrary.

Figure 1:
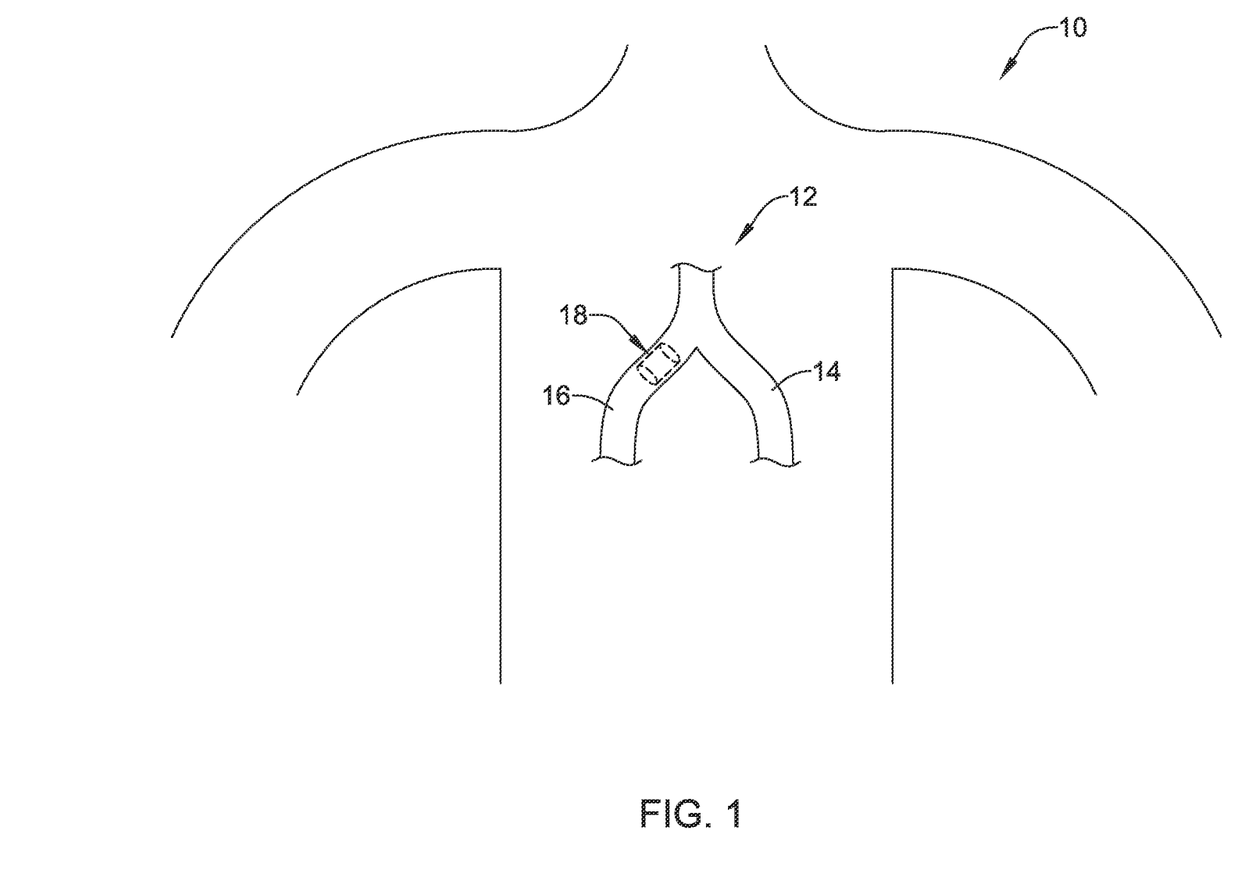
FIG. 1 is a schematic illustration of a patient, showing an airway stent disposed within the patient's trachea in accordance with an embodiment of the disclosure.

FIG. 1 provides a schematic illustration of the torso of a patient 10. The patient 10 includes a trachea 12 having a left main bronchus 14 and a right main bronchus 16 (relative to the patient's perspective). An endoprosthesis 18 may be seen in phantom, disposed within the right main bronchus 16 of the patient's trachea 12. It will be appreciated that this placement is merely for illustrative purposes, as the endoprosthesis 18 may be deployed elsewhere in the trachea 12 or even down into the bronchi (not illustrated). It will also be appreciated that while the endoprosthesis 18 is described herein as an airway stent, the endoprosthesis 18 may be deployed in a variety of other bodily lumens, including but not limited to the vascular, urinary, biliary, tracheobronchial, esophageal or renal tracts. Although illustrated as a stent, the endoprosthesis 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

A difficulty in placing an endoprosthesis in the trachea 12 is that the patient 10 may have a tendency to try and cough out the endoprosthesis 18. The human respiratory system is designed, when encountering an obstacle or other foreign object, to try to move the obstacle out of the way. This may mean pushing the object farther down, to a position of relative safety. This may also mean trying to cough it out. The human body may try to forcibly eject the object. Accordingly, and in some embodiments, the endoprosthesis 18 may be configured to help hold the endoprosthesis 18 in place within the trachea 12. The endoprosthesis 18 may be held in place frictionally, or by interference with the cords or rings present within the trachea 12.

Figure 2:
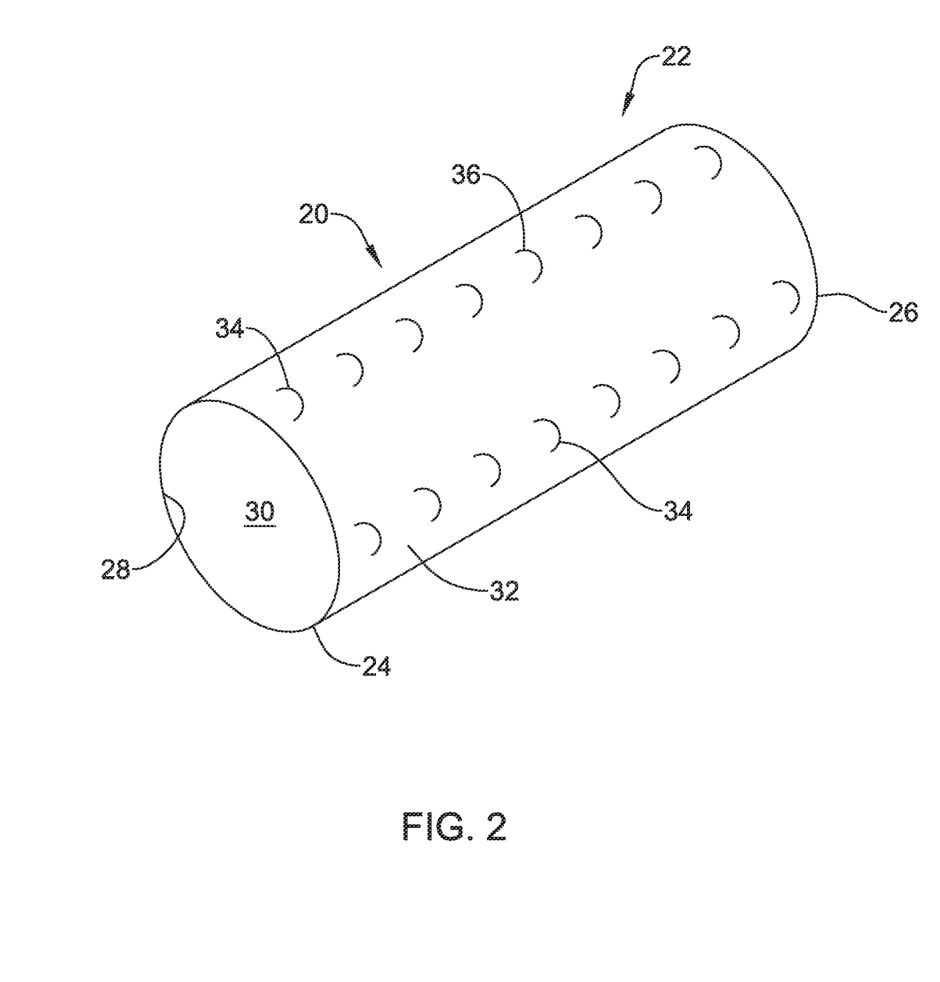
FIG. 2 is a perspective view of a stent covering in accordance with an embodiment of the disclosure.

In some embodiments, the endoprosthesis 18 may be configured to encourage tissue ingrowth, thereby securing the endoprosthesis 18 in place where desired. FIG. 2 is a perspective view of a stent covering 20 that provides for tissue ingrowth and that can be utilized as part of the endoprosthesis 18. The stent covering 20 includes a polymeric tube 22 having a first open end 24, a second open end 26 and a length extending therebetween. The polymeric tube 22 includes an inner surface 28 defining a lumen 30 and an outer surface 32. A plurality of tissue ingrowth features 34 are formed on the outer surface 32 of the polymeric tube 22. In some instances the wall of the polymeric tube 22 between the inner surface 28 and the outer surface 32 may be devoid of any openings extending therethrough. However, in other instances, the wall of the polymeric tube 22 may include one or more, or a plurality of openings extending therethrough, if desired. It will be appreciated that at least some of the plurality of tissue ingrowth features 34 include or are formed as polymeric loops 36 that extend above the outer surface 32 (i.e. extend radially outward from the outer surface 32) such that, once implanted, tissue can grow between the outer surface 32 and the polymeric loops 36. In embodiments in which the wall of the polymeric tube 22 is devoid of openings extending therethrough, the polymeric tube 22 may prevent tissue ingrowth into the lumen of the endoprosthesis 18 (i.e., prevent tissue ingrowth radially inward of the wall of the polymeric tube 22).

Figure 3A:
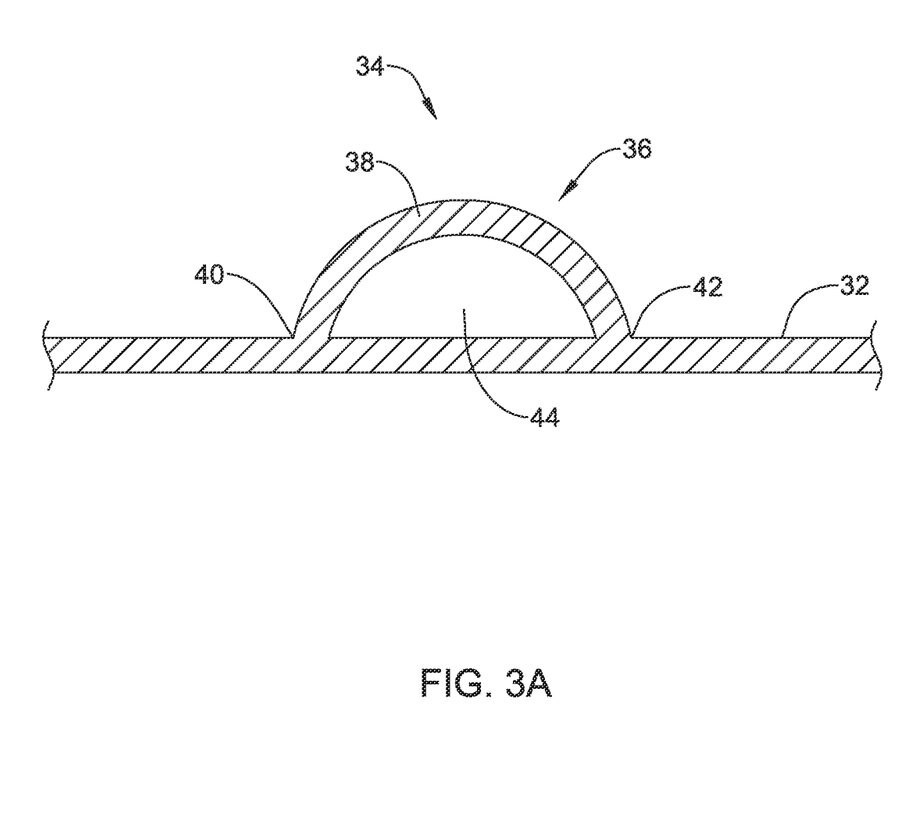
FIG. 3A is a schematic cross-sectional view of a portion of a stent covering in accordance with an embodiment of the disclosure.

Features of the polymeric loops 36 may be illustrated with respect to FIG. 3A, which is a schematic cross-sectional view taken through one of the polymeric loops 36. As can be seen, the polymeric loop 36 forms an arcuate arch having an intermediate portion 38 that is connected at a first end 40 and a second end 42 to the outer surface 32 of the polymeric tube 22. The intermediate portion 38 is not directly connected to the outer surface 32 of the polymeric tube 22, and in fact defines an open space 44 that is configured to permit tissue to grow into and through the open space 44. In some embodiments, at least some of the polymeric loops 36 may have an overall height that is about 0.5 to 3 millimeters (mm). In some embodiments, at least some of the polymeric loops 36 may have an overall width that is about 1 to 10 mm. In some embodiments, at least some of the polymeric loops 36 may have an average thickness that is about 0.1 to 3 mm. In some embodiments, the open space 44 may have a cross-sectional area of about 0.4 to 24 $mm^2$. In some embodiments, at least some of the polymeric loops 36 may have an overall length that is in the range of about 10 to about 15 millimeters (mm). In some embodiments, at least some of the polymeric loops 36 may have an overall width that is in the range of about 5 to about 7 mm. In some embodiments, at least some of the polymeric loops 36 may have an average thickness that is in the range of about 0.2 to about 0.5 mm. In some embodiments, at least some of the polymeric loops 36 may have an overall length of about 12.7 mm. In some embodiments, at least some of the polymeric loops 36 may have an overall width of about 6.4 mm. In some embodiments, at least some of the polymeric loops 36 may have an average thickness that is about 0.38 mm. In some embodiments, the open space 44 may have a cross-sectional area of about 12.9 $mm^2$.

Figure 3B:
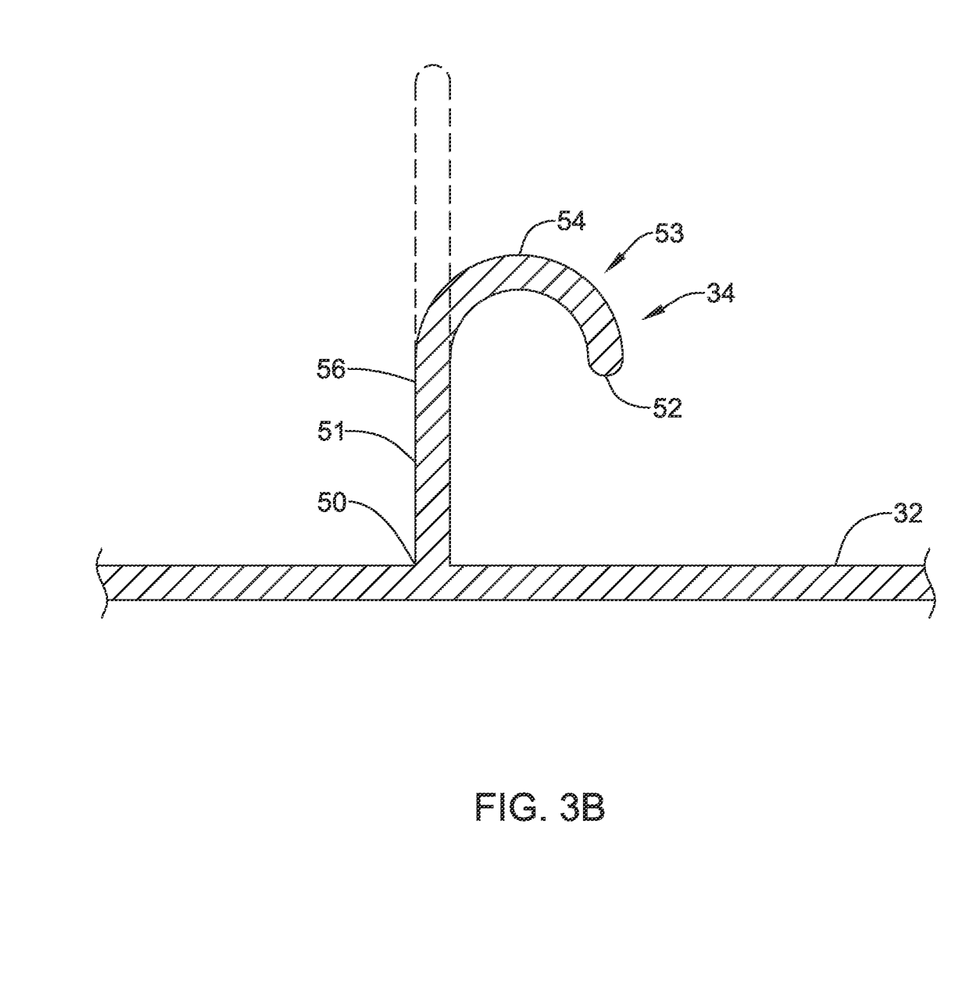
FIG. 3B is a schematic cross-sectional view of a portion of a stent covering in accordance with an embodiment of the disclosure.

In other embodiments, the tissue ingrowth features 34 may include one, two or more hooks 56 extending radially outward from the outer surface 32 of the polymeric tube 22, as shown in FIG. 3B. The hooks 56 may be instead of or in addition to the loops 36 shown in FIG. 3A. For example the hook 56 may include a base portion 51 having a first end 50 secured to the outer surface 32 of the polymeric tube 22, and an arcuate free end portion 53 having a second end 52 not directly secured to the outer surface 32 of the polymeric tube 22. In some instances, the hook 56 may be sufficiently rigid to substantially retain its hooked shape and resist applied forces during normal use while implanted in a body lumen, such as the trachea. However, if it is desired to remove the endoprosthesis 18, an applied force (e.g., a removal force) may be applied to the hook 56 which is sufficient to straighten the hook 56 (shown in phantom lines) from its natural hooked shape to a straightened shape which may facilitate detaching the hook 56 from tissue that has grown around the hook 56.

The polymeric tube 22 may be formed of any desired polymeric material. In some embodiments, the polymeric tube 22 may be formed of a biocompatible material such as polyurethane. In some embodiments, the polymeric tube 22 may be formed of a biocompatible material such as silicone. The polymeric loops 36 may be separately formed and then attached to the outer surface 32 of the polymeric tube 22. In some embodiments, the polymeric loops 36 may be integrally molded as part of the polymeric tube 22.

Figure 4:
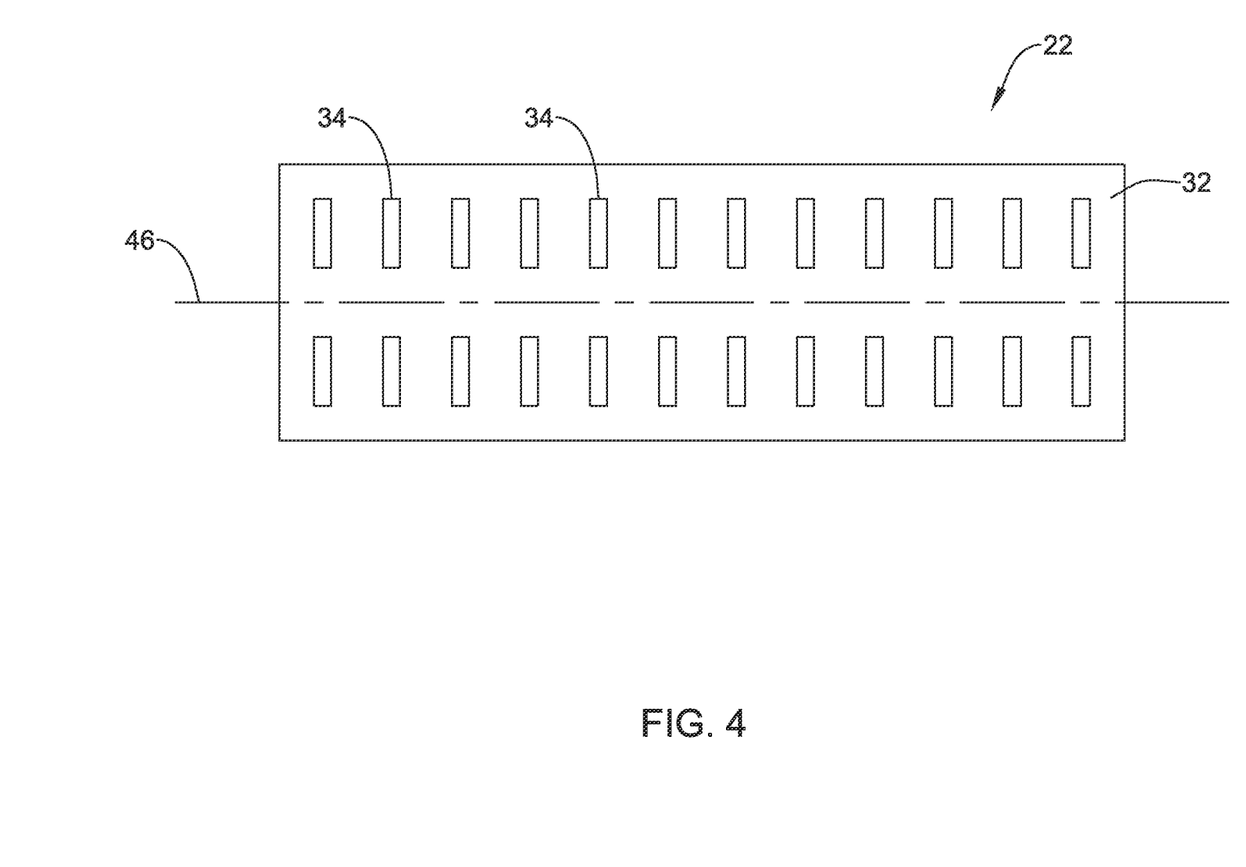
FIG. 4 is a side view of a stent covering in accordance with an embodiment of the disclosure.
Figure 5:
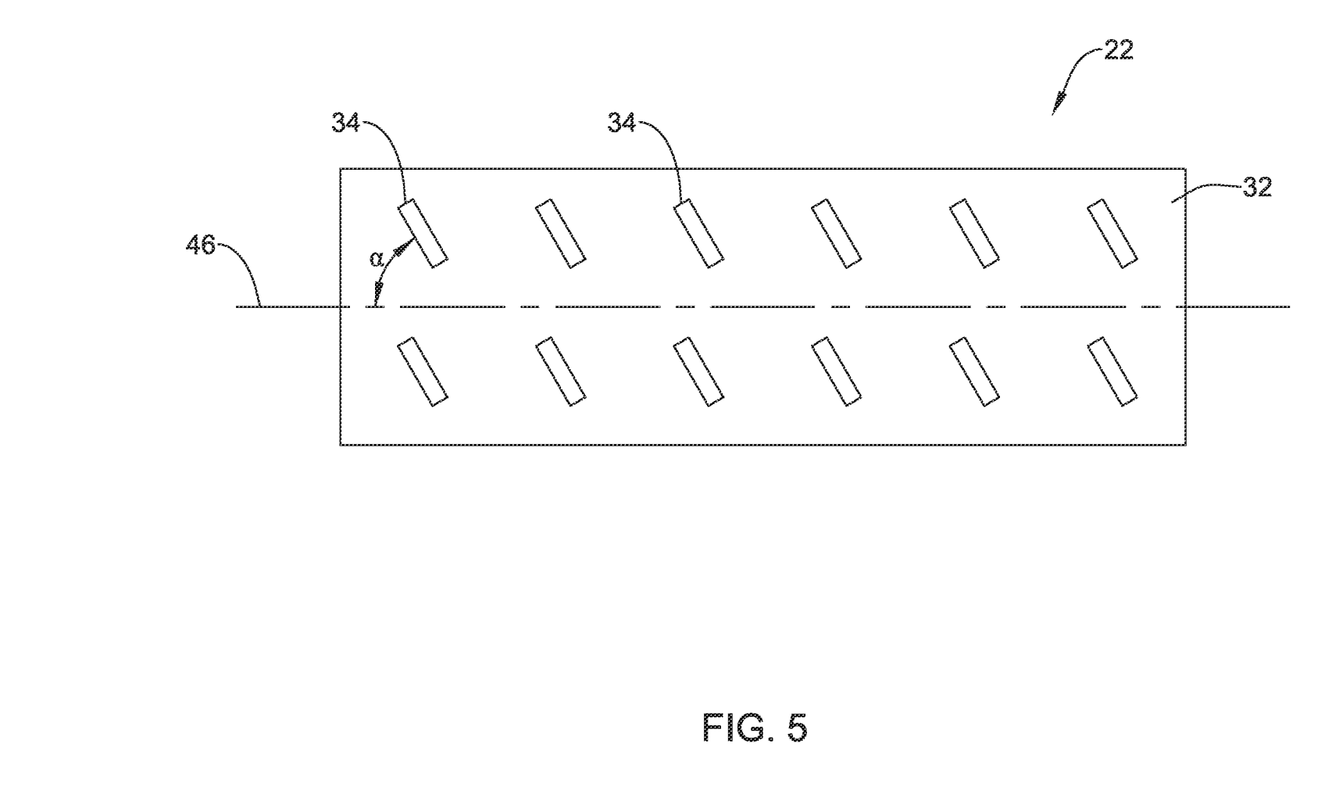
FIG. 5 is a side view of a stent covering in accordance with an embodiment of the disclosure.

The tissue ingrowth features 34 may be disposed on the outer surface 32 of the polymeric tube 22 in a variety of different orientations. In some embodiments, as illustrated for example in FIG. 4, the tissue ingrowth features 34 may be orientated transversely to the length of the polymeric tube 22, as indicated by the longitudinal axis 46. In other words, the tissue ingrowth features 34 may be oriented generally perpendicular to the longitudinal axis 46. In some embodiments, as illustrated for example in FIG. 5, the tissue ingrowth features 34 may be oriented at an acute angle α (alpha) with respect to the longitudinal axis 46. In some embodiments, α may range from 0 to 90 degrees. In some embodiments, α may range from about 10 to about 80 degrees. In some embodiments, α may range from about 10 to about 80 degrees. In some embodiments, α may range from about 20 to about 70 degrees. In some embodiments, α may range from about 30 to about 60 degrees. In some embodiments, α may range from about 40 to about 50 degrees. In some cases, some of the tissue ingrowth features 34 may be oriented at a variety of different angles relative to the longitudinal axis 46. While illustrated as two distinct rows of tissue ingrowth features 34, it will be appreciated that in some embodiments the tissue ingrowth features 34 may instead be distributed in a variety of different patterns on the outer surface 32 of the polymeric tube 22.

Figure 6:
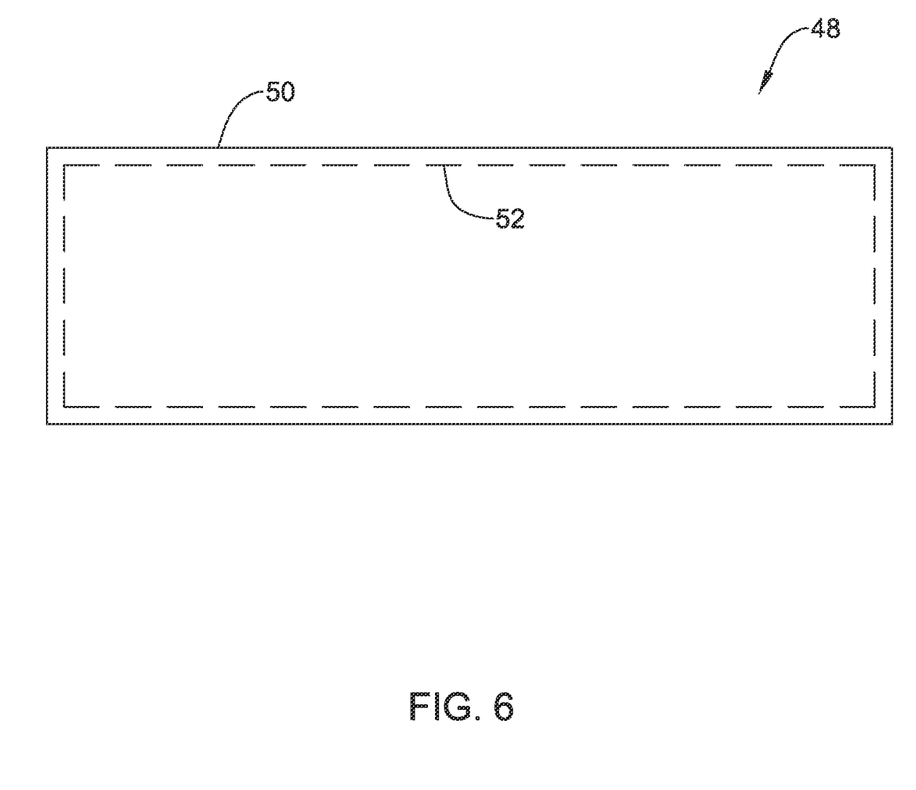
FIG. 6 is a schematic view of an airway stent in accordance with an embodiment of the disclosure.
Figure 6A:
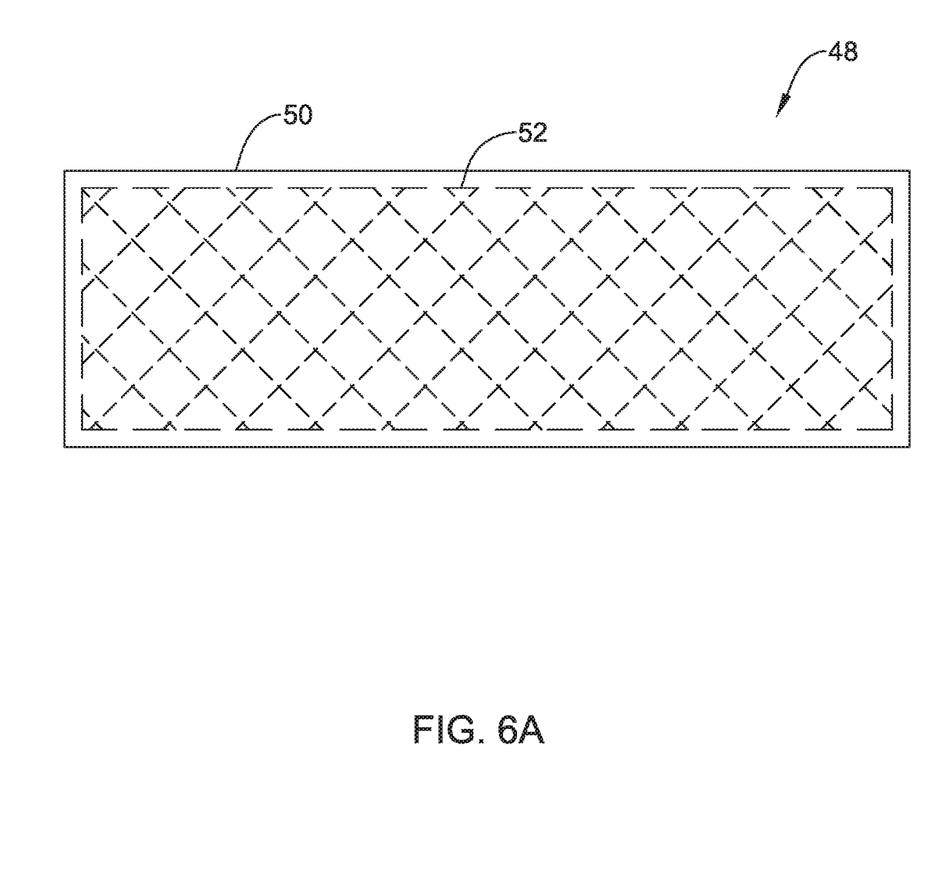
FIG. 6A is a schematic view of an airway stent in accordance with an embodiment of the disclosure.

FIGS. 6 and 6A are schematic illustrations of a stent assembly 48, in which a polymeric covering 50 is disposed over a metal stent 52, shown in phantom. While not illustrated for clarity, it should be noted that the polymeric covering 50 includes the tissue ingrowth features 34 shown with respect to FIGS. 2-5. The metal stent 52 may be considered as providing or forming a metal support structure for supporting the polymeric covering 50. In some embodiments, the metal stent 52 is expandable, but that is not required in all cases. The metal stent 52 may, for example, be a wire mesh, a braided structure (FIG. 6A), a knitted structure, an expandable scaffold, or the like. In some embodiments, the metal stent 52 may be laser cut from a metal tube, for example. In some embodiments, the stent assembly 48 may be considered as being an airway stent that is configured for long term placement within the trachea 12 of the patient 10 (FIG. 1).

In some embodiments, the metal stent 52 may be formed of any desired material, such as a biocompatible material including biostable, bioabsorbable, biodegradable or bioerodible materials. For instance, the metal stent 52 may be formed of a metallic material such as, but not limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some instances, the polymeric covering 50 may be formed separately from the stent 52, and then subsequently disposed thereover. In other instances, the polymeric covering 50 may be formed directly over the stent 52. Placement of the polymeric covering 50 over the stent 52 may cover any openings or interstices formed in the metal stent 52, such as gaps between adjacent struts or filaments of the stent 52. In such an instance, the wall of the polymeric covering 50 may prevent tissue ingrowth into the lumen of the stent 52.

In some instances, the stent 52 may be positioned through the lumen of the polymeric covering 50 and then the stent 52 may be radially expanded into contact with the polymeric covering 50. In other instances, the polymeric covering 50 may be radially stretched prior to inserting the stent 52 within the lumen of the polymeric covering 50 and then allowed to radially contract around the outer surface of the stent 52. In other instances, the polymeric covering 50 may be heat shrunk or otherwise contracted around the outer surface of the stent 52, if desired.

The tissue ingrowth features 34 may be arranged at any location along the polymeric covering 50. For example, the tissue ingrowth features 34 may be positioned proximate the opposing ends of the stent 52, while an intermediate portion is devoid of tissue ingrowth features 34. However, in other instances, the tissue ingrowth features 34 may additionally or alternatively be arranged along an intermediate portion of the polymeric covering 50, if desired.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A stent covering comprising:
   a polymeric tube having a first end, a second end and a length extending therebetween, the polymeric tube including an annular wall extending from the first end to the second end, the annular wall having an inner surface defining a lumen and an outer surface; and
   a plurality of tissue ingrowth features formed on the outer surface of the polymeric tube, at least some of the plurality of tissue ingrowth features comprising polymeric loops that extend above the outer surface such that, once implanted, tissue can grow between the outer surface and the polymeric loops, wherein at least some of the plurality of tissue ingrowth features further comprise a plurality of hooks extending radially outward from the outer surface, the hooks including a first end secured to the outer surface of the polymeric tube and an arcuate free end portion defining a single curve having a second end not directly secured to the outer surface, wherein an overall shape of each entire hook is an inverted J;
   wherein the plurality of hooks are sufficiently rigid to retain a first, hooked inverted J shape during use while implanted in a patient, the plurality of hooks being configured to be straightened to a second, substantially linear shape when a removal force is applied to the hooks, allowing detachment of the hooks from tissue that has grown around the hooks;
   wherein the annular wall is devoid of any openings extending therethrough from the outer surface to the inner surface.

2. The stent covering of claim 1, wherein at least some of the tissue ingrowth features are integrally molded as part of the polymeric tube.

3. The stent covering of claim 1, wherein the polymeric tube comprises silicone.

4. The stent covering of claim 1, wherein some of the polymeric loops comprise an arcuate arch that is connected at opposing ends to the outer surface of the polymeric tube and that has an intermediate portion that is not directly connected to the outer surface of the polymeric tube.

5. The stent covering of claim 4, wherein at least some of the polymeric loops are oriented transversely to the length of the polymeric tube.

6. The stent covering of claim 4, wherein at least some of the polymeric loops are oriented at an acute angle relative to the length of the polymeric tube.

7. The stent covering of claim 1, wherein the second end of each hook is rounded.

8. A stent assembly comprising:
   a metal stent extending from a first end to a second end, the metal stent including an inner stent surface defining a stent lumen extending therethrough, and an outer stent surface;
   a polymeric tube extending over the outer stent surface, the polymeric tube having an inner surface in contact with the outer stent surface and an outer surface; and
   a plurality of tissue ingrowth features formed on the outer surface of the polymeric tube, at least some of the plurality of tissue ingrowth features comprising a plurality of hooks extending radially outward from the outer surface of the polymeric tube, the hooks including a first end secured to the outer surface of the polymeric tube and an arcuate free end portion defining a single curve having a second end not directly secured to the outer surface, wherein an overall shape of each entire hook is an inverted J, wherein once implanted, tissue can grow around the hooks;
   wherein the plurality of hooks are sufficiently rigid to retain a first, hooked inverted J shape during use while implanted in a patient, the plurality of hooks being configured to be straightened to a second, substantially linear shape when a removal force is applied to the hooks, allowing detachment of the hooks from tissue that has grown around the hooks;
   wherein the polymeric tube prevents tissue ingrowth into the metal stent;
   wherein the plurality of tissue ingrowth features are integrally molded as part of the polymeric tube.

9. The stent assembly of claim 8, wherein the metal stent comprises an expandable metal stent.

10. The stent assembly of claim 8, wherein the polymeric tube comprises silicone.

11. The stent assembly of claim 8, wherein at least some of the plurality of tissue ingrowth features comprise polymeric loops defined by an arcuate arch that is connected at opposing ends to the outer surface of the polymeric tube and that has an intermediate portion that is not directly connected to the outer surface of the polymeric tube.

12. The stent assembly of claim 11, wherein at least some of the polymeric loops are oriented transversely to a length of the metal stent.

13. The stent assembly of claim 11, wherein at least some of the polymeric loops are oriented at an acute angle relative to a length of the metal stent.

14. The stent assembly of claim 8, wherein the second end of each hook is rounded.

15. An airway stent configured for long term placement within a patient's trachea, the airway stent comprising:
   a metal support structure extending from a first end to a second end, the metal support structure including an inner surface defining an airway stent lumen extending therethrough, and an outer surface;
   a polymeric tube extending over the outer surface, the polymeric tube including a plurality of tissue ingrowth features extending outwardly from an outer surface of the polymeric tube, at least some of the plurality of tissue ingrowth features comprising polymeric loops that extend above the outer surface of the polymeric tube such that, once implanted, tissue can grow between the outer surface and the polymeric loops, wherein at least some of the plurality of tissue ingrowth features comprise a plurality of hooks extending radially outward from the outer surface of the polymeric tube, the hooks including a first end secured to the outer surface of the polymeric tube and an arcuate free end portion defining a single curve having a second end not directly secured to the outer surface of the polymeric tube, wherein an overall shape of each entire hook is an inverted J;

wherein the plurality of hooks are sufficiently rigid to retain a first, hooked inverted J shape during use while implanted in a patient, the plurality of hooks being configured to be straightened to a second, substantially linear shape when a removal force is applied to the hooks, allowing detachment of the hooks from tissue that has grown around the hooks;

wherein the polymeric tube is devoid of any openings extending therethrough between the outer surface of the polymeric tube and an inner surface of the polymeric tube, thereby preventing tissue ingrowth into the airway stent lumen;

wherein the plurality of tissue ingrowth features are integrally molded as part of the polymeric tube.

16. The airway stent of claim 15, wherein the polymeric tube comprises silicone.

17. The airway stent of claim 15, wherein the each of the polymeric loops comprise an arcuate arch that is connected at opposing ends to the outer surface of the polymeric tube and that has an intermediate portion that is not directly connected to the outer surface of the polymeric tube.

18. The airway stent of claim 15, wherein at least some of the polymeric loops are oriented transversely to a length of the metal support structure.

19. The airway stent of claim 15, wherein at least some of the polymeric loops are oriented at an acute angle relative to a length of the metal support structure.

20. The airway stent of claim 15, wherein the second end of each hook is rounded.

* * * * *